United States Patent

Hirsch et al.

[11] Patent Number: 5,496,300
[45] Date of Patent: Mar. 5, 1996

[54] COUPLING DEVICE FOR A LEG URINAL

[76] Inventors: Michael P. Hirsch; Patricia Hirsch, both of 18 Pine Dr., Oyster Bay, N.Y. 11791

[21] Appl. No.: 296,500

[22] Filed: Aug. 26, 1994

[51] Int. Cl.[6] .......................................... A61B 1/00
[52] U.S. Cl. .................. 604/327; 604/905; 604/280; 137/614.05
[58] Field of Search ...................... 604/322–327, 604/329, 905, 280; 137/614.03, 614.04, 614.05; 285/319

[56] References Cited

U.S. PATENT DOCUMENTS

| | | | |
|---|---|---|---|
| 3,500,859 | 3/1970 | Pearson | 137/614.05 |
| 3,529,599 | 9/1970 | Folkman | |
| 4,319,573 | 3/1982 | Whitlock | 604/323 |
| 4,511,358 | 4/1985 | Johnson, Jr. | 604/327 |
| 4,569,348 | 2/1986 | Hasslinger | 604/179 |
| 4,828,554 | 5/1989 | Griffin | 604/350 |
| 4,846,816 | 7/1989 | Manfredi | 604/323 |
| 4,870,975 | 10/1989 | Cronk et al. | 128/249 |
| 4,938,747 | 7/1990 | Wallace | 604/317 |
| 5,052,725 | 10/1991 | Meyer et al. | |
| 5,316,041 | 5/1994 | Ramacier, Jr. et al. | |

OTHER PUBLICATIONS

Colder Products Company, In–line Plastic Tubing Connections Advertising Sheet, 1994.
Colder Products Company, MPC Series Coupling Brochure, 1994.
Colder Products Company, Quick Couplings and Fittings for Plastic Tubing Brochure, 1995.

Primary Examiner—Randall L. Green
Assistant Examiner—Mark O. Polutta
Attorney, Agent, or Firm—Collard & Roe

[57] ABSTRACT

A coupling device for a urinal including a urine collection bag and a flexible tube connected to a user's catheter. A quick release coupling readily connects and disconnects the flexible tube to the urine collection bag to provide a fluid passageway upon connection. The coupling closes both the tube opening and the bag opening upon disconnection to prevent fluid from spilling out and to avoid contaminants from entering the flexible tube.

13 Claims, 2 Drawing Sheets

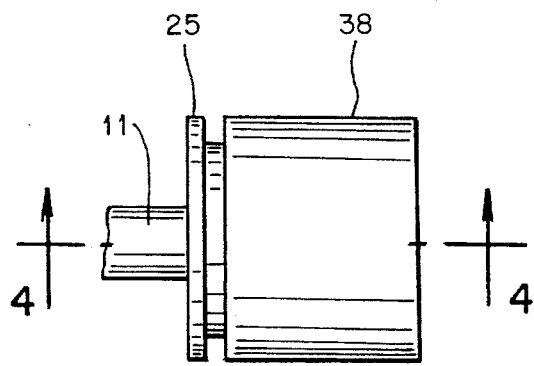
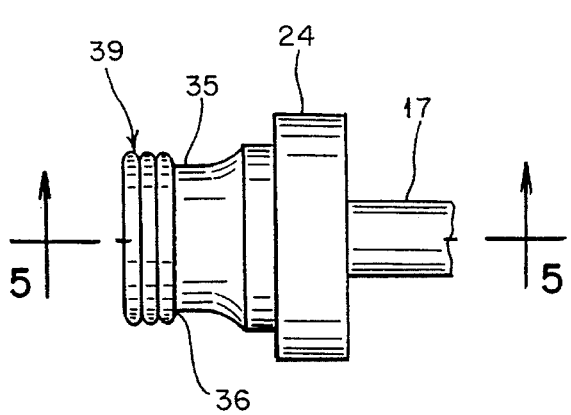
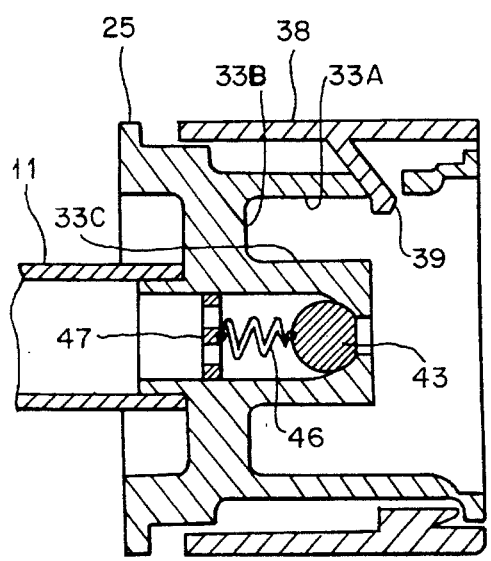
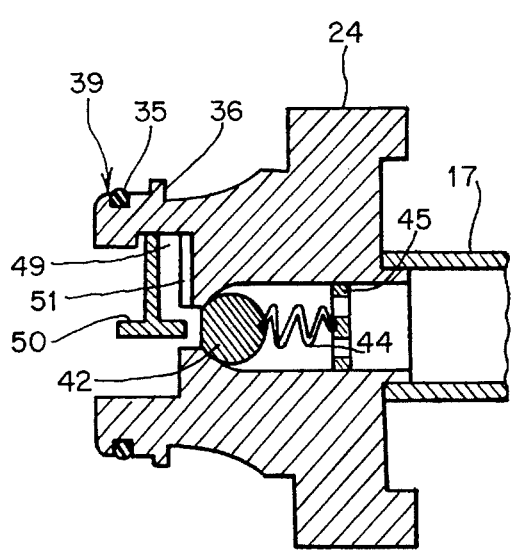

COUPLING DEVICE FOR A LEG URINAL

BACKGROUND OF THE INVENTION

1. Field of the Invention

The present invention relates to urine collection containers, such as leg urinal bags and the like, associated with user-worn catheters. More particularly, it relates to a coupling device for such urinals permitting flow into the container while connected and sealing both ends of the coupling upon disconnection.

2. Prior Art

Many persons are compelled to be fitted with catheters, either permanently or temporarily, for drainage of the contents of the bladder. Catheters are of two basic types, either internally connected to the bladder so that relatively small quantities of urine are emptied more or less continuously, or externally connected whereby relatively large quantities of urine are excreted from time to time. In either case, flow of the liquid into the container must be unimpeded and backflow must be avoided.

The problems inherent in catherized urine drainage and storage systems are well known. Thus, for example, blockage of forward flow can results in stagnation, bacterial growth and infection. Backflow of already excreted urine can have similar dangerous results, in addition to unpleasant accidental staining of clothing or bedding. Where the system includes a collection bag worn by the user, problems of hygiene and odor are always present unless disconnection and cleaning of the bag and attachments are readily achievable. U.S. patents related to collection bags include U.S. Pat. No. 4,870,975, U.S. Pat. No. 4,511,358, U.S. Pat. No. 4,938,747, U.S. Pat. No. 4,569,348, U.S. Pat. No. 4,955,879 and U.S. Pat. No. 4,846,816.

In order to overcome certain of these deficiencies, the inlet openings on urine collection bags have been equipped with an anti-reflux valve in the lower part of a drip housing which provides an air break in the urine column, as described in U.S. Pat. No. 3,529,599. Also, U.S. Pat. No. 4,828,554 to Griffin discloses a one-way valve located within a collar at the top of the urine collection bag. Although these devices help to prevent the backflow of urine, a serious problem still exists with spilling urine when the bag is disconnected for cleaning or replacement, especially if the bag is at or near capacity. Accordingly, it would be desirable to have a coupling device which allows urine to flow unimpeded into the collection bag when connected, but seals both ends of the connection when the bag is disconnected for cleaning or replacement.

SUMMARY OF THE INVENTION

It is therefore an object of the present invention to overcome the drawbacks of the prior art and to provide a quick release coupling device which allows unimpeded flow from the catheter into the collection bag when connected.

It is a further object of the present invention to provide a coupling device which seals both ends of the connection when the collection bag is disconnected.

It is a further object of the present invention to provide highly visible and easily attachable and detachable leg straps for the collection bag.

It is yet another object of the present invention to provide a chemical test strip on the urine collection bag to automatically test the contents upon draining.

These and other related objects are achieved according to the invention by a coupling device for a urinal including a urine collection bag with liquid inlet opening and a flexible tube having an upstream end operationally connectable to a user's catheter, and a downstream end. A quick-release coupling for readily connecting and disconnecting the downstream end from the inlet opening is provided. The coupling provides a fluid passageway from the tube to the bag inlet opening upon connection and closes both the inlet opening and the downstream end upon disconnection to prevent fluid spillage therefrom and to avoid contaminants from entering the flexible tube. The quick-release coupling includes a first coupling member securely connected to the liquid inlet opening and a second coupling member securely connected to the downstream end of the flexible tube. The coupling members have opposed mating surfaces that form a liquid seal upon connection around the fluid passageway to contain the fluid. A gasket is mounted on one of the mating surfaces to seal against the other mating surface.

The first coupling member includes a recess and the second coupling member includes a clasp to engage the recess and securely connect the coupling members together. The clasp is biased toward the recess, and during connection, the first coupling member displaces the clasp against the biasing force until the clasp is aligned with and snaps into the recess. The device further includes release means on the second coupling member to retract the clasp to disconnect the coupling members. The release means consists of an axially displaceable collar connected to the clasp.

Each coupling member includes an aperture and a spring loaded closure member that closes the aperture during disconnection. An arm is positioned and configured to displace both closure members and open the apertures upon connection to establish the fluid passageway around the closure members and through the apertures. The urine collection bag includes a liquid outlet opening for draining the collection bag. A chemical test strip is attached to the collection bag adjacent the liquid outlet opening, so that the chemical test strip is automatically wetted during draining of the collection bag to conduct a chemical test. A color chart is provided on the urine collection bag adjacent the chemical test strip for comparison with the wetted test strip.

The device further includes a plurality of glow-in-the-dark straps each having a first end connected to the bag and a spaced opposite second free end. The free ends are provided with hook and loop fasteners for encircling and releasably connecting the bag to a user's leg.

In an alternate embodiment, there is provided a device for releasably coupling a tube, connected to a user's catheter to a urine collection bag having an inlet opening. The device comprises a quick-release coupling for readily and releasably connecting the tube to the inlet opening. The coupling allows urine to flow from the catheter through the tube and inlet opening into the bag during connection. The coupling further seals the tube and the inlet opening upon disconnection to prevent urine spillage therefrom and contaminants from entering therein.

The quick-release coupling is forcibly snap fitted together to place the catheter and tube in fluid communication with the bag and includes release means to disconnect the coupling. The coupling includes an exterior and an inner central fluid passageway. Fluid sealing is provided concentrically around the central fluid passageway to prevent spillage during connection. The release means includes an axially displaceable collar concentrically mounted on the coupling exterior.

BRIEF DESCRIPTION OF THE DRAWINGS

Other objects and features of the present invention will become apparent from the following detailed description considered in connection with the accompanying drawings which disclose an embodiment of the present invention. It should be understood, however, that the drawings are designed for the purpose of illustration only and not as a definition of the limits of the invention.

In the drawings, wherein similar reference characters denote similar elements throughout the several views:

FIG. 2 is a side-elevational view of a first coupling member;

FIG. 3 is a side elevational view of the second coupling member;

FIG. 4 is a cross-sectional view of the first coupling member taken along line 4—4 from FIG. 2;

FIG. 5 is a cross-sectional view of the second coupling member taken along the line 5—5 from FIG. 3.

DETAILED DESCRIPTION OF PREFERRED EMBODIMENT

Figure 1:
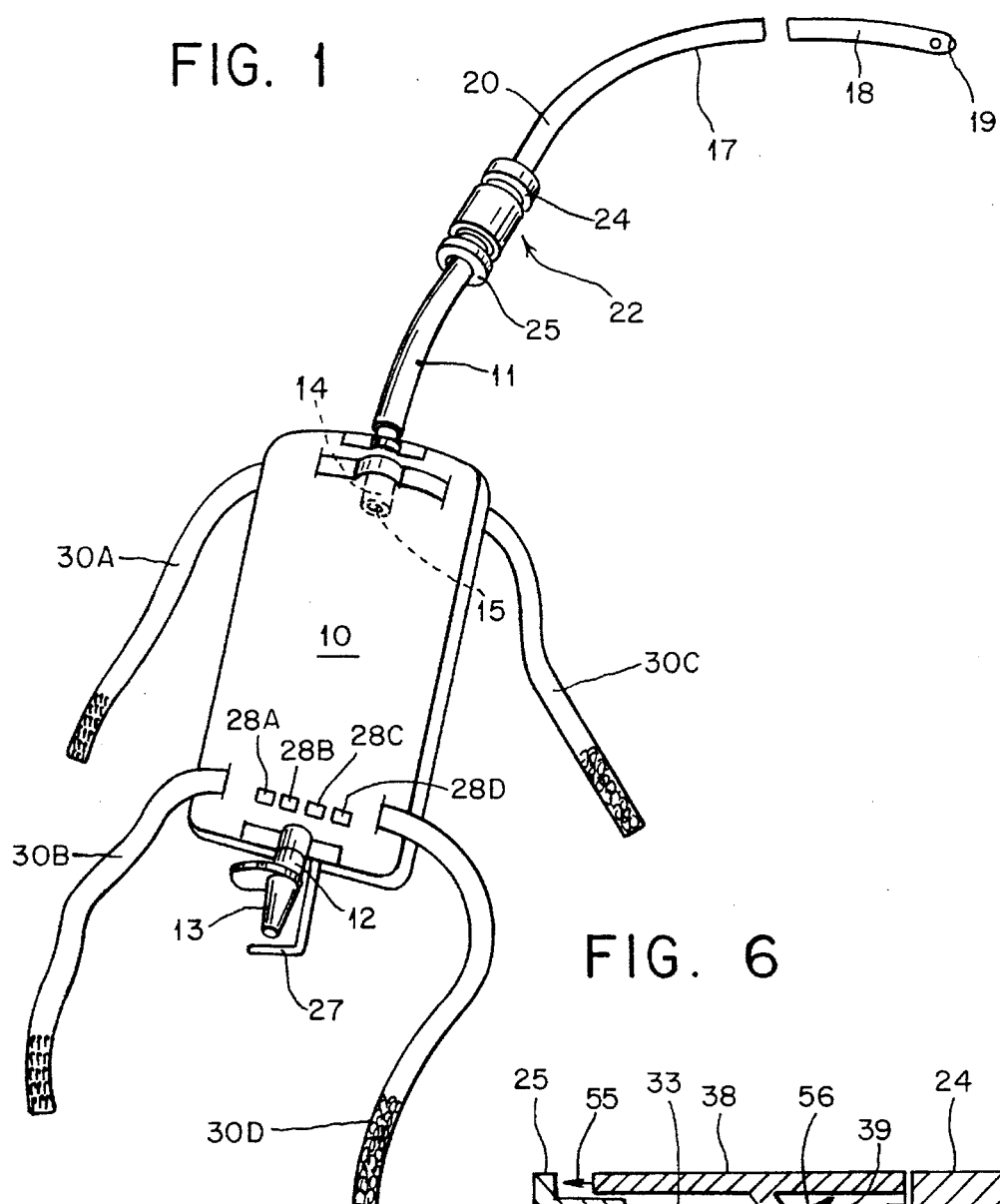
FIG. 1 is a perspective view of a urine collection bag with a catheter connected by an embodiment of the coupling device according to the invention.

Referring now in detail to the drawings and, in particular, FIG. 1, there is shown a urinal collection bag 10 equipped with a liquid inlet line 11 and a liquid outlet line 12. Liquid inlet line 11 is coupled to a drip housing 14 which is fitted within the tubular neck of bag 10. Drip housing 14 has a one-way disc valve or anti-reflux valve 15 at its lower end. Drip housing 14 and valve 15 provide an air break in the urine column from the patient and prevent urine from backing up into the patient's bladder from bag 10. The drip housing is further described in U.S. Pat. No. 3,529,599 to Folkman, the subject matter of which is incorporated herein by reference thereto.

A tube 17 has an upstream end 18 connected with a catheter 19. Tube 17 also includes a downstream end 20 which is attached to line 11 via a coupling device 22. Coupling device 22 includes a first coupling member 24 which is securely connected to downstream end 20 of tube 17 and a second coupling member 25 which is securely connected to line 11. Alternatively, second coupling member 25 is incorporated into drip housing 14, thus eliminating the need for line 11. When connected, coupling device 22 places tube 17 in fluid communication with line 11 allowing liquid to flow from catheter 19 unimpeded through tube 17 and line 11 into bag 10. Coupling device 22, when connected, provides a continuous fluid pathway from catheter 19 to bag 10, i.e. it allows line 11 and tube 17 to function as a single, continuous uninterrupted tube or line. The first coupling member 24 may be quickly and easily disconnected from second coupling member 25 to drain, clean or replace bag 10.

Bag 10 is easily drained through liquid outlet line 12 by removing a cap 13. A chemical test strip 27 is attached to a lower end of bag 10 or liquid outlet line 12 or cap 13. Upon removal of cap 13, the liquid draining from bag 10 impinges upon test strip 27. Chemical test strip 27 is used to detect a certain pH or certain components within urine as a screening test for urinary tract infection (UTI) or other conditions, for example. After test strip 27 has been wetted, it is compared with color charts 28A, 28B, 28C and 28D. Additional instructions may be printed on bag 10 to inform the individual conducting the test regarding the test results. For example, if the wetted test strip 27 has no color change as per color chart 28A, then the condition is normal. If the wetted test strip 27 turns the color of color charts 28B, 28C or 28D, the individual would be instructed to administer medication to the patient or contact their physician. If test strip 27 is a litmus strip it will turn pink or red in acids indicating an abnormal condition. Ordinarily, liquid outlet line 12 and test strip 27 can be folded up parallel to bag 10 out of the way until needed. Following the draining of bag 10, test strip 27 may be again folded up to bring it in close proximity to the color charts. After use, test strip 27 may be torn off and discarded. Several test strips may be attached to bag 10, line 12 or cap 13, so that the screening test can be performed each time the bag is drained.

Straps 30A, 30B, 30C and 30D extend off opposing sides of bag 10 to secure it to the patient's leg. The straps are made from or coated with a glow-in-the-dark material, for example, neon glow straps so that the patient can easily see them in the dark. The ends of strap 30A and 30B are provided with a hook material and the ends of strap 30C and 30D are provided with a loop material, for example. Straps 30A and 30C can be wrapped around the leg and easily connected together at a comfortable tension as determined by the patient. Similarly, straps 30B and 30D can be wrapped around the leg and attached to each other.

FIGS. 2 and 3 show first coupling member 24 disconnected from second coupling member 25. First coupling member 24 has a male mating surface 34 provided with an O-ring 35. Alternatively, a gasket may be located on the end of male mating surface 34 facing second coupling member 25. A recess 36 is disposed just behind male mating surface 34. Second coupling member 25 includes a collar 38 which will be further explained below.

Figure 6:
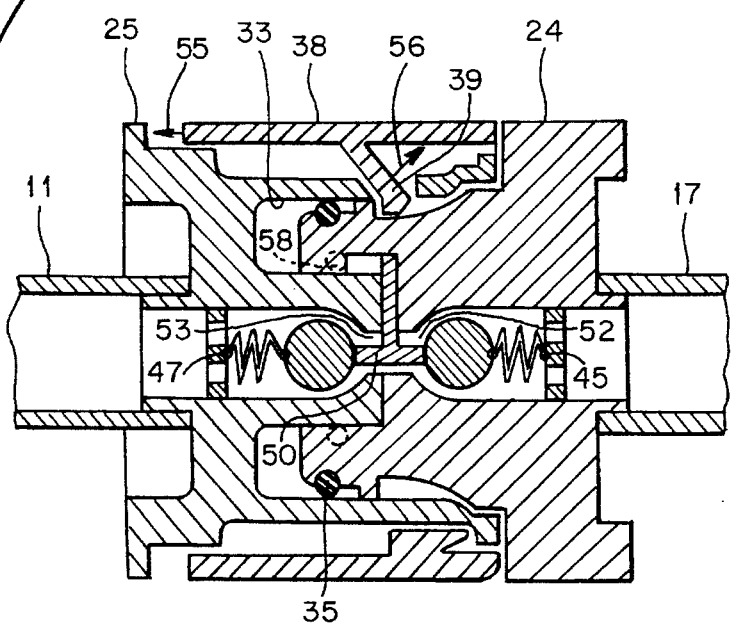
FIG. 6 is a cross-sectional view of the first and second coupling members connected together.

FIGS. 4 and 5 show a first closure member 42 and a second closure member 43 which are biased toward each other by a first spring 44 and a second spring 46. The springs are secured to a first slotted plate 45 and a second slotted plate 47, respectively. Second coupling member 25 includes a female mating surface 33A against which O-ring 35 seals. Male mating surface 34 may also seal against female mating surfaces 33B or 33C. A resilient clasp 39 is connected to collar 38 through an aperture. The bevelled surface of male mating surface 34 biases clasp 39 outwardly as it slides past. Clasp 39 then snaps into recess 36, as can be seen in FIG. 6. A T-shaped arm 50 is movable within a groove 49 and may be accommodated within a slot 51.

As can be seen in FIG. 6, arm 50 displaces first closure member 42 and second closure member 43 away from each other to place first aperture 52 and second aperture 53 in fluid communication with each other. Fluid can now pass from tube 17, through first slotted plate 45 around the first spring and first closure member through first aperture 52. Fluid then exits first coupling member 24 and enters second coupling member 25. The fluid flows through second aperture 53 around second closure member 43 and second spring 46 through second slotted plate 47 into liquid inlet line 11. FIG. 6 also shows O-ring 35 tightly sealed against female mating surface 33. Alternatively, O-ring 58, shown in phantom line, may be employed to seal against surface 33C.

In order to release first coupling member 24 from second coupling member 25, collar 38 is retracted in axial direction 55. This causes clasp 39 to swing outwardly in radial direction 56 as it abuts the edge of the aperture in which it resides. Once clasp 39 is fully retracted out of recess 36 and clears male mating surface 34, first coupling member 24 can be withdrawn from second coupling member 25. Upon disconnection, springs 44 and 46 bias closure members 42 and 43, respectively, into apertures 52 and 53 sealing off tube 17 and line 11. Thus, when the coupling members are disconnected, urine cannot drip out of tube 17 or out of bag 10 through line 11.

It should be understood that the coupling members may be interchanged on line 11 in tube 17. In addition, the specific structure shown for sealing and opening the aperture is merely exemplary and many other configurations may be employed within the scope of the invention. Finally, the sealing between the opposed mating surfaces and the manner in which the coupling members are snapped together may also be greatly varied in keeping within the scope of the invention.

While a single embodiment of the present invention has been shown and described, it is to be understood that many changes and modifications may be made thereunto without departing from the spirit and scope of the invention as defined in the appended claims.

What is claimed is:

1. A coupling device for a urinal comprising:
   a urine collection bag with a liquid inlet line;
   a flexible tube having an upstream end operationally connectable to a user's catheter and a downstream end; and
   quick-release coupling means for readily connecting and disconnecting said downstream end from said inlet line, said coupling means providing a fluid passageway from said tube to said bag inlet line upon connection and closing both said inlet line and said downstream end of said tube upon disconnection to prevent fluid spillage therefrom and to avoid contaminants from entering said tube, said quick release coupling means having an axial and a radial direction and comprising:
   (a) a first coupling member securely connected to said liquid inlet line and having a first aperture and a first spring loaded closure member for closing the first aperture upon disconnection;
   (b) a second coupling member securely-connected to said downstream end of said flexible tube and having a second aperture and a second spring loaded closure member for closing the second aperture upon disconnection; and
   (c) a radially-inwardly extending arm attached to one of said coupling members for positively displacing said spring loaded closure members away from the respective apertures upon connection.

2. The coupling device according to claim 1, wherein said coupling members having opposed mating surfaces that form a liquid seal upon connection around the fluid passageway to contain the fluid.

3. The coupling device according to claim 2, comprising a gasket mounted on one of said mating surfaces that seals against the other mating surface.

4. The coupling device according to claim 3, wherein said first coupling member includes a recess and said second coupling member includes a resilient clasp to engage the recess and securely connect said coupling members together.

5. The coupling device according to claim 4, wherein said clasp is biased toward the recess, and during connection said first coupling member displaces said clasp against the biasing force until said clasp is aligned with and snaps into the recess.

6. The coupling device according to claim 5, comprising release means on said second coupling member to retract said clasp to disconnect said coupling members.

7. The coupling device according to claim 6, wherein said release means comprises an axially-displaceable collar connected to said clasp.

8. A coupling device for a urinal comprising:
   a urine collection bag with a liquid inlet line, a liquid outlet opening for draining said collection bag, and a chemical test strip attached to said collection bag adjacent said liquid outlet opening, so that said chemical test strip is automatically wetted during draining of said collection bag to conduct a chemical test;
   a flexible tube having an upstream end operationally connectable to a user's catheter and a downstream end; and
   quick-release coupling means for readily connecting and disconnecting said downstream end from said inlet line, said coupling means providing a fluid passageway from said tube to said bag inlet line upon connection and closing both said inlet line and said downstream end of said tube upon disconnection to prevent fluid spillage therefrom and to avoid contaminants from entering said tube, said quick-release coupling means comprising a first coupling member securely connected to said liquid inlet line, and a second coupling member securely connected to said downstream end of said flexible tube, said coupling members having opposed mating surfaces that form a liquid seal upon connection around the fluid passageway to contain the fluid;
   said first coupling member including a recess and said second coupling member including a resilient clasp to engage the recess and securely connect said coupling members together, said clasp being biased toward the recess, and during connection said first coupling member displacing said clasp against the biasing force until said clasp is aligned with and snaps into the recess;
   release means on said second coupling member to retract said clasp to disconnect said coupling members, said release means comprising an axially-displaceable collar connected to said clasp;
   each coupling member including an aperture and a spring loaded closure member that closes the aperture during disconnection;
   a gasket mounted on one of said mating surfaces for sealing against the other mating surface; and
   an arm positioned and configured to displace both closure members and open the apertures upon connection to establish said fluid passageway around said closure members and through the apertures.

9. The coupling device according to claim 8, comprising a plurality of glow-in-the-dark straps each having a first end connected to said bag and a spaced opposite second free end, wherein said free ends are provided with hook and loop fasteners adapted for encircling and releasably connecting said bag to a user's leg.

10. The coupling device according to claim 8, comprising a color chart on said urine collection bag adjacent said chemical test strip for comparison with said wetted test strip.

11. A device for coupling to a urinal and automatically conducting a chemical test, the device comprising:
    a urine collection bag with a liquid inlet line, a liquid outlet opening for draining said collection bag, and a chemical test strip attached to said collection bag so that said chemical test strip is automatically wetted during use of said collection bag to conduct a chemical test;

a flexible tube having an upstream end operationally connectable to a user's catheter and a downstream end; and quick-release coupling means for readily connecting and disconnecting said downstream end from said inlet line, said coupling means providing a fluid passageway from said tube to said bag inlet line upon connection and closing both said inlet line and said downstream end of said tube upon disconnection to prevent fluid spillage therefrom and to avoid contaminants from entering said tube.

12. The coupling device according to claim 11, comprising a color chart on said urine collection bag adjacent said chemical test strip for comparison with said wetted test strip.

13. The coupling device according to claim 11, comprising a plurality of glow-in-the-dark straps each having a first end connected to said bag and a spaced opposite second free end, wherein said free ends are provided with hook and loop fasteners adapted for encircling and releasably connecting said bag to a user's leg.

* * * * *